United States Patent [19]

Inoue et al.

[11] Patent Number: 5,042,461
[45] Date of Patent: Aug. 27, 1991

[54] HORN USED IN AN ULTRASONIC SURGICAL OPERATING INSTRUMENT

[75] Inventors: Naohiko Inoue; Yasuo Noguchi, both of Yokohama, Japan

[73] Assignee: Sumitomo Bakelite Company Limited, Tokyo, Japan

[21] Appl. No.: 350,352

[22] Filed: May 11, 1989

[30] Foreign Application Priority Data

May 17, 1988 [JP] Japan .............. 63-64020[U]
Apr. 5, 1989 [JP] Japan .............. 1-39629[U]

[51] Int. Cl.$^5$ .................................. A61B 17/32
[52] U.S. Cl. ....................... 128/24 A; 604/22; 604/266; 606/169
[58] Field of Search .......... 239/102.2, 589.1, 590; 128/24 A, 303.14, 305, 328; 433/119; 606/45, 127, 128, 167, 169, 170; 604/22, 266, 268, 902

[56] References Cited

U.S. PATENT DOCUMENTS

| 994,780 | 6/1911 | Olney | 239/590 |
|---|---|---|---|
| 1,983,601 | 12/1934 | Conn | 604/22 |
| 2,012,363 | 8/1935 | Vogel | 606/45 |
| 2,815,757 | 12/1957 | Piar | 606/45 |
| 3,240,431 | 3/1966 | Hug et al. | 239/589.1 |
| 3,526,219 | 7/1967 | Balamuth | 433/119 |
| 3,531,048 | 9/1970 | Hughes | 239/589.1 |
| 3,554,443 | 1/1971 | Hughes | 239/589.1 |
| 3,841,568 | 10/1974 | Broad | 239/590 |
| 4,045,859 | 9/1977 | Cooley et al. | 29/451 |
| 4,265,621 | 5/1981 | McVey | 604/268 |
| 4,398,910 | 8/1983 | Blake et al. | 604/266 |
| 4,747,820 | 5/1988 | Hornlein et al. | 604/22 |
| 4,756,478 | 7/1988 | Endo et al. | 239/102.2 |
| 4,767,404 | 8/1988 | Renton | 604/268 |
| 4,799,622 | 1/1989 | Ishikawa et al. | 239/102.2 |

FOREIGN PATENT DOCUMENTS

| 0001718 | 5/1979 | European Pat. Off. . |
|---|---|---|
| 2906823 | 9/1980 | Fed. Rep. of Germany ... 239/102.2 |
| 3707921 | 9/1987 | Fed. Rep. of Germany . |
| 0002709 | 1/1978 | Japan .................. 239/102.2 |

Primary Examiner—Lee S. Cohen
Assistant Examiner—K. M. Pfaffle
Attorney, Agent, or Firm—Browdy and Neimark

[57] ABSTRACT

A horn used in an ultrasonic surgical operating instrument for crushing and removing organic tissue comprises a horn body vibrated by and ultrasonic vibration source for crushing the organic tissue, a removing passage extending through the horn body, through which the crushed tissue is removed outside, a bulkhead disposed in the removing passage, and at least one through hole formed in the bulkhead. The bulkhead and the hole cooperate with each other to reduce a cross-sectional area of the removing passage.

5 Claims, 2 Drawing Sheets

FIG. 5A
FIG. 5B
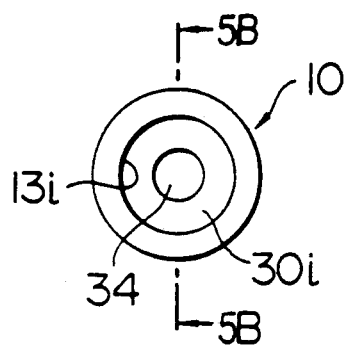
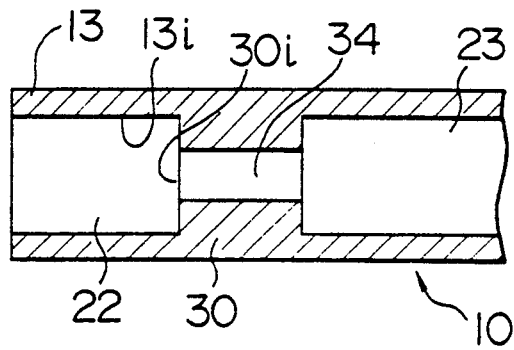
FIG. 6A
FIG. 6B
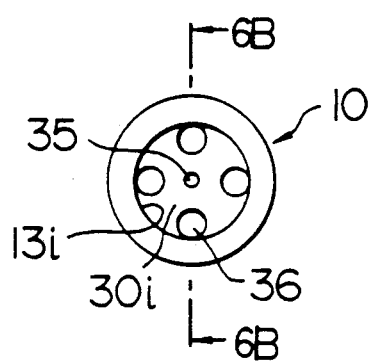
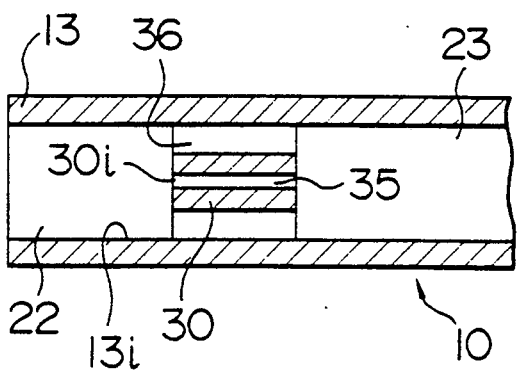
FIG. 7A
PRIOR ART
FIG. 7B
PRIOR ART
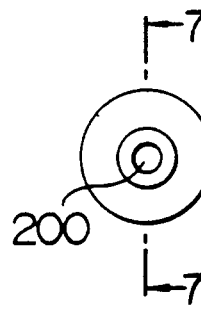
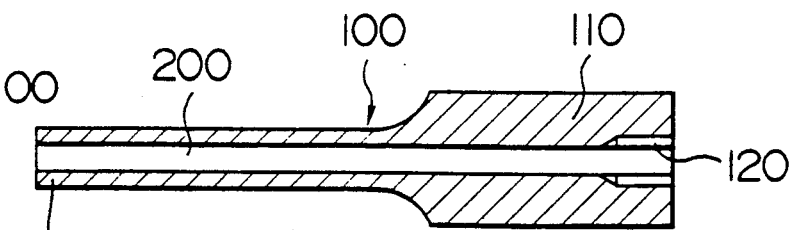

HORN USED IN AN ULTRASONIC SURGICAL OPERATING INSTRUMENT

FIELD OF THE INVENTION AND RELATED ART STATEMENT

The present invention relates to a horn used in an ultrasonic surgical operating instrument, and more particularly to a horn for crushing and removing organic tissue.

Recently, an ultrasonic surgical instrument, e.g. an ultrasonic operating scalpel, has been used in various surgical operations. The ultrasonic surgical instrument utilizes a mechanical vibration caused by an ultrasonic source for crushing and emulsifying organic tissue, and removes the crushed tissue outside. A horn in the ultrasonic surgical instrument is connected at one end thereof with the ultrasonic source. Mechanical vibration caused by the ultrasonic source is transmitted to an operating portion of the horn located on the other end portion thereof. The operating portion of the horn vibrates to crush the tissue, which abuts on the organic tissue to be treated. The crushed tissue is removed outside of the horn through a passage formed in the horn. The passage generally opens at the other end of the horn and has a uniform cross-sectional area. Accordingly, it becomes the problem that the tissue is insufficiently and roughly crushed by the operating portion and then coarse crushed tissue pieces clog the passage.

OBJECT AND SUMMARY OF THE INVENTION

An object of the present invention is to provide a horn capable of efficiently crushing and removing organic tissue without clogging the passage formed in the horn.

To this end, according to the present invention, provided is a horn for crushing and removing organic tissue comprising, a horn body vibrated by ultrasonic vibration source, passage means extending through the horn body, and means for reducing a cross-sectional dimension of the passage means.

Other objects and the advantages of the present invention will become apparent from the following description of the preferred embodiments explained with referring to the accompanying drawings attached hereto.

BRIEF DESCRIPTION OF THE DRAWINGS

FIG. 5A is a side view of a horn according to a fifth embodiment;

FIG. 5B is a fragmentary sectional view of the horn taken along the line 5B—5B in FIG. 5A;

FIG. 6A is a side view of a horn according to a sixth embodiment;

FIG. 6B is a fragmentary sectional view of the horn taken along the line 6B—6B in FIG. 6A;

FIG. 7A is a side view of a horn according to a prior art; and

FIG. 7B is a sectional view of the horn taken along the line 7B—7B in FIG. 7A.

DETAILED DESCRIPTION OF THE PREFERRED EMBODIMENTS

Figure 1A:
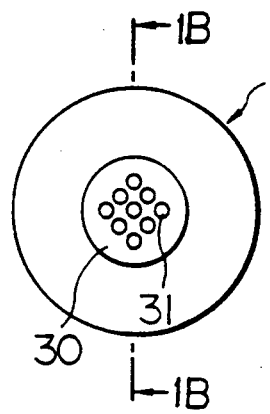
FIG. 1A is a side view of a horn according to a first embodiment of the present invention.
Figure 1B:
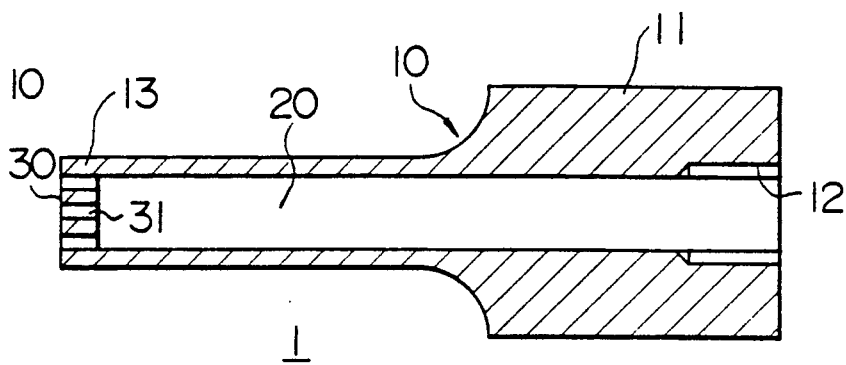
FIG. 1B is a sectional view of the horn taken along the line 1B—1B in FIG. 1A.

In a first embodiment shown in FIGS. 1A and 1B, a horn 1 includes a horn body 10 having at one end portion thereof a radially enlarged part 11. The horn body 10 may be made of metal having a corrosion resistance, such as titanium or aluminium alloy and stainless steel. The horn body 10 is provided therein with a straight suction passage 20 extending axially therethrough. The horn body 10 is to be connected at one end thereof with an ultrasonic transducer which acts as an ultrasonic vibration source. The connection between the horn body 10 and the transducer is to be conducted by means of screw coupling through a thread portion 12 formed in an inner wall of the passage 20. On the connection, the transducer is so connected to the horn body 10 that a through passage formed in the transducer coincides with the passage 20.

A bulkhead 30 is located in the passage 20 and is integrally formed with an end of the other end portion 13 of the horn body 10. The bulkhead 30 is provided with a plurality of small through holes 31. These holes 31 serve to reduce a cross-sectional area of the passage 20. The bulkhead 30 has a thickness of 0.5 mm to 25 mm, preferably 1 mm to 10 mm.

An operation of the above-mentioned embodiment will be described hereinunder.

At first, the horn 1 is so positioned that the end portion 13, so called an operating portion 13, abuts on the organic tissue to be treated. Thereafter, a driving power is supplied to the transducer to reciprocate or vibrate the horn body 1. Accordingly the operating portion 13 of the horn body 10 crushes and emulsifies the organic tissue. Simultaneously cleaning liquid agent is usually applied towards the operating portion 13. The horn 1 removes the crushed and emulsified organic tissue, and the cleaning liquid agent or a body fluid outside of the horn 1 through the passage 20.

In this embodiment, since the cross-sectional area of the passage 20 is once reduced by the holes 31 formed in the bulkhead 30, the only fine crushed tissue can pass into the passage 20 through the holes 31. No coarse crushed tissue pieces can pass through the holes 31 to clog the passage 20. Further the bulkhead 30 serves to increase a contact area of the horn body 10 against the tissue. Therefore crushing efficiency of the horn 1 is extremely raised. To the contrary, in the prior art, as shown in FIGS. 7A and 7B, since the passage 200 is uniform in a cross-sectional area thereof, coarse crushed tissue pieces can be sucked into the passage 200 to clog it.

The material of the horn body 10 may not be limited to ones described above. Another material is applicable, which has a sufficient strength against the ultrasonic vibration having a propagation speed of 1000 m/s to 6000 m/s. These are, for example, the carbon fiber reinforced metal composed of metal (e.g. aluminum) and the carbon fiber, and a carbon fiber reinforced plastic composed of plastic (e.g. polysulfone) and carbon fiber. Further graphite is also applicable.

In the first embodiment, a plurality of small holes 31 are provided in the bulkhead 30. However, even though a single hole is provided in the bulkhead 30 instead of the holes 31, the same advantages can be enjoyed.

Figure 2A:
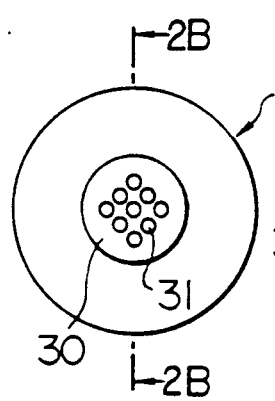
FIG. 2A is a side view of a horn according to a second embodiment.
Figure 2B:
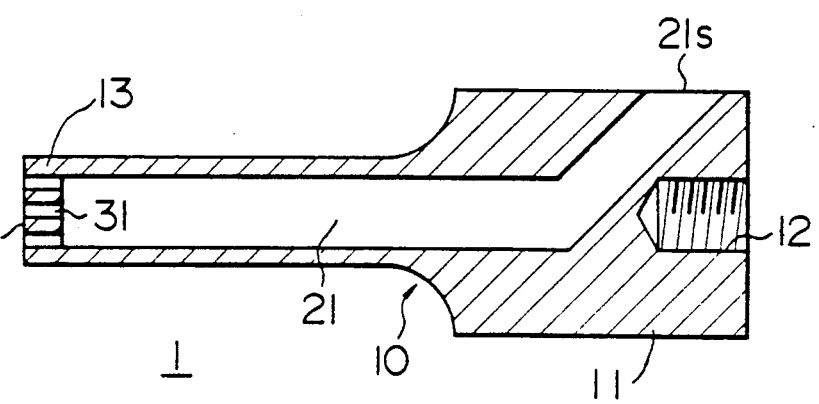
FIG. 2B is a sectional view of the horn taken along the line 2B—2B in FIG. 2A.

Referring to FIGS. 2A and 2B, a second embodiment has a bent suction passage 21 opening at a side wall of the enlarged part 11. The crushed and emulsified organic tissue is removed outside through a metal or a plastic tube communicated to the side wall opening 21s. The ultrasonic transducer is to be attached to one end of the enlarged part 11 of the horn body 10 through a thread portion 12 formed therein.

Figure 3A:
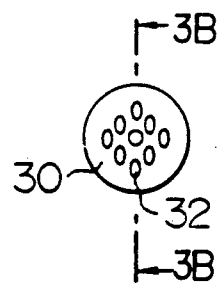
FIG. 3A is a side view of a horn according to a third embodiment.
Figure 3B:
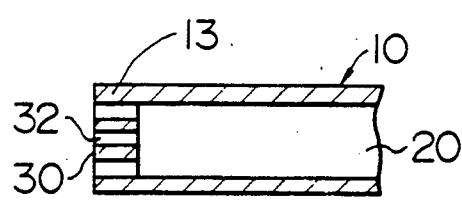
FIG. 3B is a fragmentary sectional view of the horn taken along the line 3B—3B in FIG. 3A.
Figure 4A:
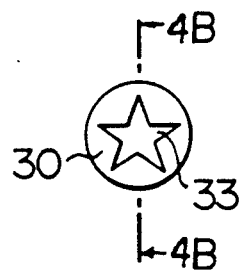
FIG. 4A is a side view of a horn according to a fourth embodiment.
Figure 4B:
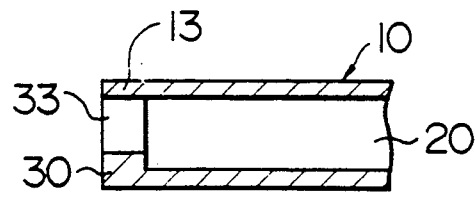
FIG. 4B is a fragmentary sectional view of the horn taken along the line 4B—4B in FIG. 4A.

It should be noted that a cross-sectional shape of the hole in the bulkhead is not limited to a circular. As shown in FIGS. 3A and 3B, a plurality of holes each having a elliptic cross-section are applicable. Further a polygonal cross-sectional aperture or a poly-edgings cross-sectional aperture 33 is also applicable as shown in FIGS. 4A and 4B.

Referring to FIGS. 5A and 5B, another embodiment has a bulkhead 30 disposed apart somewhat from the operating portion 13, which divides the passage into two parts 22 and 23. The bulkhead 30 is provided therein with an aperture 34 which extends through the bulkhead 30 and having a cross-sectional area smaller than that of the passage. According to this embodiment, a further fine crushing of the tissue can be obtained. Namely, the organic tissue is roughly crushed first by the operating portion 13 and received within the passage part 22. In the passage part 22, the coarse crushed tissue pieces collide with an end face 30i of the the bulkhead 30 to be further crushed to fine pieces. The fine pieces of the tissue pass into the passage part 23 through the aperture 34, without clogging of the passage part 23.

When the fragile tissue is crushed, it may be possible for the fragile tissue to scatter around to contaminate or damage the neighboring tissue. In this embodiment, an inner wall 13i of the operating portion 13 prevents the pieces of tissue crushed by the bulkhead 30 from scattering outwards. Accordingly, if the present horn is applied to crush fragile tissue, e.g. calcium laden tissue, the resultant crushed pieces are prevented from scattering and therefore damage to neighboring tissue is avoided.

Though an axial length of the passage part 22 varies according to an amplitude of ultrasonic vibration source supplied to the horn, the length is 0.1 mm to 30 mm, preferably 1 mm to 15 mm.

It should be noted that a plurality of small apertures may be formed in the bulkhead 30 instead of a single aperture. In this case, the same advantages as the above mentioned can be also enjoyed. The dimensions of the apertures 35 and 36 may be different from each other as shown in FIGS. 6A and 6B.

What is claimed is:

1. A horn used in an ultrasonic surgical operating instrument for crushing and removing organic tissue, said horn comprising:
    a horn body for crushing said organic tissue which is ultrasonically vibrated;
    passage means extending through said horn body, through which the crushed tissue is removed outside;
    means provided within said passage means for reducing a cross-sectional dimension of said passage means;
    said reducing means comprising a bulkhead disposed in said passage means and aperture means for axially extending through said bulkhead;
    wherein said bulkhead is disposed in a midway portion in said passage means.

2. A horn according to claim 1, wherein said aperture means includes at least two through holes.

3. A horn according to claim 2, wherein said holes have circular or elliptical cross-sections.

4. A horn according to claim 2, wherein said holes have polygonal cross-sections.

5. A horn according to claim 2, wherein said holes have poly-edgings cross-sections.

* * * * *